United States Patent
Alquist et al.

(10) Patent No.: US 11,278,744 B2
(45) Date of Patent: Mar. 22, 2022

(54) SYSTEMS AND METHODS TO ACCOUNT FOR TILT OF A RADIATION MEASUREMENT SYSTEM

(71) Applicant: Sun Nuclear Corporation, Melbourne, FL (US)

(72) Inventors: Erik Alquist, Melbourne, FL (US); William E. Simon, Melbourne, FL (US)

(73) Assignee: SUN NUCLEAR CORPORATION, Melbourne, FL (US)

( * ) Notice: Subject to any disclaimer, the term of this patent is extended or adjusted under 35 U.S.C. 154(b) by 358 days.

(21) Appl. No.: 16/582,445

(22) Filed: Sep. 25, 2019

(65) Prior Publication Data
US 2020/0101327 A1    Apr. 2, 2020

Related U.S. Application Data

(60) Provisional application No. 62/738,613, filed on Sep. 28, 2018.

(51) Int. Cl.
*A61N 5/10*        (2006.01)
*G01T 7/00*        (2006.01)

(52) U.S. Cl.
CPC ............ *A61N 5/1075* (2013.01); *G01T 7/005* (2013.01); *A61N 2005/1076* (2013.01)

(58) Field of Classification Search
CPC .......... A61N 5/1075; A61N 2005/1076; G01T 7/005
See application file for complete search history.

(56) References Cited

U.S. PATENT DOCUMENTS

| 759,608 A | 5/1904 | Harper |
| 1,239,145 A | 9/1917 | Wantz |
| (Continued) | | |

FOREIGN PATENT DOCUMENTS

| CA | 2718408 | 9/2009 |
| DE | 102009039345 A1 | 3/2011 |
| (Continued) | | |

OTHER PUBLICATIONS

International Search Report and Written Opinion dated Oct. 2, 2020, PCT Application No. PCT/US2020/041458.
(Continued)

*Primary Examiner* — Blake C Riddick
(74) *Attorney, Agent, or Firm* — Pillsbury Winthrop Shaw Pittman LLP

(57) ABSTRACT

Systems, methods, and computer program products that are configured to account for tilt of a radiation measurement system are disclosed. In one embodiment, a system includes a scanning system with a radiation detector, the scanning system configured to enable movement of the radiation detector. The system also includes a non-transitory machine-readable medium storing instructions which, when executed by at least one programmable processor, cause the at least one programmable processor to perform various operations including moving the radiation detector through a first, second, and third vertical calibration path and recording a first, second, and third radiation detector response within 3 cm of a water surface, and controlling the scanning system to move the radiation detector through at least one measurement path that takes into account a scanning system tilt, the at least one measurement path determined based on at least the first, second, and third radiation detector responses.

11 Claims, 9 Drawing Sheets

(56) References Cited

U.S. PATENT DOCUMENTS

| | | | |
|---|---|---|---|
| 2,818,510 | A | 12/1957 | Verse |
| 3,033,985 | A | 5/1962 | Ben |
| 3,267,728 | A | 8/1966 | Solomons |
| 3,327,213 | A | 6/1967 | Wald, Jr. |
| 3,394,258 | A | 7/1968 | Schleiger |
| 3,433,953 | A | 3/1969 | Sweet |
| 3,665,762 | A | 5/1972 | Domen |
| 3,783,251 | A | 1/1974 | Pavkovich |
| 3,790,794 | A | 2/1974 | Murray |
| 3,980,885 | A | 9/1976 | Steward |
| 4,058,832 | A | 11/1977 | Vagi |
| 4,063,097 | A | 12/1977 | Barrett |
| 4,107,531 | A | 8/1978 | Garratt |
| 4,157,472 | A | 6/1979 | Barrett |
| 4,312,224 | A | 1/1982 | Domen |
| 4,450,440 | A | 5/1984 | White |
| 4,455,609 | A | 6/1984 | Inamura |
| 4,613,754 | A | 9/1986 | Vinegar |
| 4,729,099 | A | 3/1988 | Iverson |
| 4,765,749 | A | 8/1988 | Bourgade |
| 4,777,442 | A | 10/1988 | Rosenthal |
| 4,887,287 | A | 12/1989 | Cobben |
| 5,099,505 | A | 3/1992 | Seppi |
| 5,160,337 | A | 11/1992 | Cosman |
| 5,262,649 | A | 11/1993 | Antonuk |
| 5,388,142 | A | 2/1995 | Morris |
| 5,394,452 | A | 2/1995 | Swerdloff |
| 5,596,653 | A | 1/1997 | Kurokawa |
| 5,602,892 | A | 2/1997 | Llacer |
| 5,621,214 | A * | 4/1997 | Sofield .............. G01T 1/185 250/375 |
| 5,622,187 | A | 4/1997 | Carol |
| 5,627,367 | A | 5/1997 | Sofield |
| 5,635,709 | A | 6/1997 | Sliski |
| 5,640,436 | A | 6/1997 | Kawai |
| 5,661,310 | A | 8/1997 | Jones |
| 5,704,890 | A | 1/1998 | Bliss |
| 5,712,482 | A | 1/1998 | Gaiser |
| 5,873,826 | A | 2/1999 | Gono |
| 5,988,875 | A | 11/1999 | Gershfeld |
| 6,038,283 | A | 3/2000 | Carol |
| 6,125,335 | A | 9/2000 | Simon |
| 6,131,690 | A | 10/2000 | Galando |
| 6,148,272 | A | 11/2000 | Bergstrom |
| 6,175,761 | B1 | 1/2001 | Frandsen |
| 6,207,952 | B1 * | 3/2001 | Kan .............. A61N 5/1048 250/252.1 |
| 6,257,552 | B1 | 7/2001 | Crow |
| 6,261,219 | B1 | 7/2001 | Meloul |
| 6,301,329 | B1 | 10/2001 | Surridge |
| 6,322,249 | B1 | 11/2001 | Wofford |
| 6,345,114 | B1 | 2/2002 | Mackie |
| 6,364,529 | B1 | 4/2002 | Dawson |
| 6,398,710 | B1 | 6/2002 | Ishikawa |
| 6,516,046 | B1 | 2/2003 | Froehlich |
| 6,535,574 | B1 | 3/2003 | Collins |
| 6,535,756 | B1 | 3/2003 | Simon |
| 6,552,347 | B1 | 4/2003 | Dimcovski |
| 6,560,311 | B1 | 5/2003 | Shepard |
| 6,594,336 | B2 | 7/2003 | Nishizawa |
| 6,609,626 | B2 | 8/2003 | Young |
| 6,609,826 | B1 | 8/2003 | Fujii |
| 6,626,569 | B2 | 9/2003 | Reinstein |
| 6,636,622 | B2 | 10/2003 | Mackie |
| 6,648,503 | B2 | 11/2003 | Tanaka |
| 6,712,508 | B2 | 3/2004 | Nilsson |
| 6,788,759 | B2 | 9/2004 | Op De Beek |
| 6,799,068 | B1 | 9/2004 | Hartmann |
| 6,810,107 | B2 | 10/2004 | Steinberg |
| 6,810,108 | B2 | 10/2004 | Clark |
| 6,833,707 | B1 | 12/2004 | Dahn |
| 6,839,404 | B2 | 1/2005 | Clark |
| 6,853,702 | B2 | 2/2005 | Renner |
| 6,888,919 | B2 | 5/2005 | Graf |
| 6,904,119 | B2 | 6/2005 | Oikawa |
| 6,904,125 | B2 | 6/2005 | Van Dyk |
| 6,904,162 | B2 | 6/2005 | Robar |
| 6,974,254 | B2 | 12/2005 | Paliwal |
| 6,990,368 | B2 | 1/2006 | Simon |
| 6,992,309 | B1 | 1/2006 | Petry |
| 7,016,454 | B2 | 3/2006 | Warnberg |
| 7,065,812 | B2 | 6/2006 | Newkirk |
| 7,076,023 | B2 | 7/2006 | Ghelmansarai |
| 7,098,463 | B2 | 8/2006 | Adamovics |
| 7,116,749 | B2 | 10/2006 | Besson |
| 7,125,163 | B2 | 10/2006 | Eigler |
| 7,127,028 | B2 | 10/2006 | Sendai |
| 7,127,030 | B2 | 10/2006 | Tamegai |
| 7,142,634 | B2 | 11/2006 | Engler |
| 7,193,220 | B1 | 3/2007 | Navarro |
| 7,221,733 | B1 | 5/2007 | Takai |
| 7,233,688 | B2 | 6/2007 | Ritt |
| 7,234,355 | B2 | 6/2007 | Dewangan |
| 7,298,820 | B2 | 11/2007 | Nelson |
| 7,339,159 | B2 | 3/2008 | Juh |
| 7,349,523 | B2 | 3/2008 | Jenkins |
| 7,352,840 | B1 | 4/2008 | Nagarkar |
| 7,371,007 | B2 | 5/2008 | Nilsson |
| 7,386,089 | B2 | 6/2008 | Endo |
| 7,420,160 | B2 | 9/2008 | Delaperriere |
| 7,453,976 | B1 | 11/2008 | Yin |
| 7,455,449 | B2 | 11/2008 | Nishimura |
| 7,471,765 | B2 | 12/2008 | Jaffray |
| 7,515,681 | B2 | 4/2009 | Ebstein |
| 7,579,608 | B2 | 8/2009 | Takahashi |
| 7,605,365 | B2 | 10/2009 | Chen |
| 7,636,419 | B1 | 12/2009 | Nelson |
| 7,668,292 | B1 | 2/2010 | Bose |
| 7,734,010 | B2 | 6/2010 | Otto |
| 7,750,311 | B2 | 7/2010 | Daghighian |
| 7,766,903 | B2 | 8/2010 | Blumenkranz |
| 7,773,723 | B2 | 8/2010 | Nord |
| 7,778,383 | B2 | 8/2010 | Koehler |
| 7,778,392 | B1 | 8/2010 | Berman |
| 7,778,680 | B2 | 8/2010 | Goode, Jr. |
| 7,782,998 | B2 | 8/2010 | Langan |
| 7,945,022 | B2 | 5/2011 | Nelms |
| 8,044,359 | B2 | 10/2011 | Simon |
| 8,093,549 | B2 | 1/2012 | Navarro |
| 8,130,905 | B1 | 3/2012 | Nelms |
| 8,136,773 | B2 | 3/2012 | Schmutzer |
| 8,147,139 | B2 | 4/2012 | Papaioannou |
| 8,218,718 | B1 | 7/2012 | Van Herk |
| 8,235,530 | B2 | 8/2012 | Maad |
| 8,242,458 | B2 | 8/2012 | Rinecker |
| 8,321,179 | B2 | 11/2012 | Simon |
| 8,325,878 | B2 | 12/2012 | McNutt |
| 8,430,564 | B2 | 4/2013 | Simmons |
| 8,457,713 | B2 | 6/2013 | Kagermeier |
| 8,474,794 | B2 | 7/2013 | Liljedahl |
| 8,536,547 | B2 | 9/2013 | Maurer |
| 8,541,756 | B1 | 9/2013 | Treas |
| 8,605,857 | B1 | 12/2013 | Renner |
| 8,632,448 | B1 | 1/2014 | Schulte |
| 8,726,814 | B1 | 5/2014 | Matteo |
| 8,794,899 | B2 | 8/2014 | Cozza |
| 8,833,709 | B2 | 9/2014 | Weng |
| 8,840,304 | B2 | 9/2014 | Perez Zarate |
| 8,840,340 | B2 | 9/2014 | Eisenhower |
| 8,874,385 | B2 | 10/2014 | Takayanagi |
| 8,927,921 | B1 | 1/2015 | Nelms |
| 9,050,460 | B2 | 6/2015 | Hildreth |
| 9,097,384 | B1 | 8/2015 | Simon |
| 9,310,263 | B2 | 4/2016 | Thoen |
| 9,463,336 | B2 | 10/2016 | Nelms |
| 9,480,861 | B2 | 11/2016 | Kapatoes |
| 9,561,388 | B2 | 2/2017 | Hildreth |
| 9,586,060 | B2 | 3/2017 | Seuntjens |
| 9,750,955 | B2 | 9/2017 | McNutt |
| 9,895,557 | B2 | 2/2018 | Seuntjens |
| 10,755,823 | B2 | 8/2020 | Carette |
| 2001/0042841 | A1 | 11/2001 | Lyons |
| 2002/0077545 | A1 | 6/2002 | Takahashi |
| 2002/0080912 | A1 | 6/2002 | Mackie |

(56) References Cited

U.S. PATENT DOCUMENTS

| | | |
|---|---|---|
| 2003/0043879 A1 | 3/2003 | Tanaka |
| 2003/0043960 A1 | 3/2003 | Op De Beek |
| 2003/0138077 A1 | 7/2003 | Lee |
| 2003/0231740 A1 | 12/2003 | Paliwal |
| 2004/0066880 A1 | 4/2004 | Oikawa |
| 2004/0068182 A1 | 4/2004 | Misra |
| 2004/0096033 A1 | 5/2004 | Seppi |
| 2004/0113094 A1 | 6/2004 | Lyons |
| 2004/0120560 A1 | 6/2004 | Robar |
| 2004/0158145 A1 | 8/2004 | Ghelmansarai |
| 2004/0211917 A1 | 10/2004 | Adamovics |
| 2004/0228435 A1 | 11/2004 | Russell |
| 2004/0251419 A1 | 12/2004 | Nelson |
| 2005/0013406 A1 | 1/2005 | Dyk |
| 2005/0077459 A1 | 4/2005 | Engler |
| 2005/0111621 A1 | 5/2005 | Riker |
| 2006/0002519 A1 | 1/2006 | Jenkins |
| 2006/0033044 A1 | 2/2006 | Gentry |
| 2006/0184124 A1 | 8/2006 | Cowan |
| 2006/0203964 A1 | 9/2006 | Nyholm |
| 2006/0203967 A1 | 9/2006 | Nilsson |
| 2006/0266951 A1 | 11/2006 | Fritsch |
| 2007/0041497 A1 | 2/2007 | Schnarr |
| 2007/0041499 A1 | 2/2007 | Lu |
| 2007/0053492 A1 | 3/2007 | Kidani |
| 2007/0071169 A1 | 3/2007 | Yeo |
| 2007/0081629 A1 | 4/2007 | Yin |
| 2007/0086577 A1 | 4/2007 | Kobayashi |
| 2007/0172020 A1* | 7/2007 | Nambu ............ A61B 6/583 378/4 |
| 2007/0195930 A1 | 8/2007 | Kapatoes |
| 2008/0031406 A1 | 2/2008 | Yan |
| 2008/0049896 A1 | 2/2008 | Kuduvalli |
| 2008/0049898 A1 | 2/2008 | Romesberg, III |
| 2008/0091388 A1 | 4/2008 | Failla |
| 2008/0103834 A1 | 5/2008 | Reiner |
| 2008/0118137 A1 | 5/2008 | Chen |
| 2008/0260368 A1 | 10/2008 | Chang |
| 2008/0292055 A1 | 11/2008 | Boone |
| 2009/0003512 A1 | 1/2009 | Pouliot |
| 2009/0067576 A1 | 3/2009 | Maltz |
| 2009/0090870 A1 | 4/2009 | Ahnesjo |
| 2009/0175418 A1 | 7/2009 | Sakurai |
| 2009/0217999 A1 | 9/2009 | Becker |
| 2009/0227841 A1 | 9/2009 | Miyako |
| 2009/0250618 A1 | 10/2009 | Simon |
| 2009/0252292 A1 | 10/2009 | Simon |
| 2009/0326365 A1* | 12/2009 | Goldenberg ......... A61B 34/30 600/411 |
| 2010/0008467 A1 | 1/2010 | Dussault |
| 2011/0022360 A1 | 1/2011 | Simon |
| 2011/0051893 A1 | 3/2011 | McNutt |
| 2011/0085716 A1 | 4/2011 | Chefd Hotel |
| 2011/0096906 A1 | 4/2011 | Langeveld |
| 2011/0158386 A1 | 6/2011 | Payne |
| 2011/0204262 A1 | 8/2011 | Pu |
| 2011/0210258 A1 | 9/2011 | Black |
| 2011/0248188 A1 | 10/2011 | Brusasco |
| 2011/0278444 A1 | 11/2011 | Navarro |
| 2011/0306864 A1 | 12/2011 | Zarate |
| 2012/0014618 A1 | 1/2012 | Sun |
| 2012/0025105 A1 | 2/2012 | Brown |
| 2012/0025826 A1* | 2/2012 | Zhou ............ G01R 33/56518 324/309 |
| 2012/0230462 A1 | 9/2012 | Robar |
| 2012/0292517 A1 | 11/2012 | Izaguirre |
| 2012/0305793 A1 | 12/2012 | Schiefer |
| 2012/0326057 A1 | 12/2012 | Remeijer |
| 2013/0048883 A1 | 2/2013 | Simon |
| 2013/0258105 A1 | 10/2013 | Jozsef |
| 2013/0303902 A1 | 11/2013 | Smith |
| 2014/0016754 A1 | 1/2014 | Sugiyama |
| 2014/0064445 A1 | 3/2014 | Adler |
| 2014/0073834 A1 | 3/2014 | Hildreth |
| 2014/0077098 A1 | 3/2014 | Tachikawa |
| 2014/0094642 A1 | 4/2014 | Fuji |
| 2014/0105355 A1 | 4/2014 | Toimela |
| 2014/0263990 A1 | 9/2014 | Kawrykow |
| 2015/0080634 A1 | 3/2015 | Huber |
| 2015/0087879 A1 | 3/2015 | Nelms |
| 2015/0108356 A1 | 4/2015 | Seuntjens |
| 2015/0124930 A1 | 5/2015 | Verhaegen |
| 2015/0238778 A1 | 8/2015 | Hildreth |
| 2015/0283403 A1 | 10/2015 | Kapatoes |
| 2015/0309193 A1 | 10/2015 | Kozelka |
| 2015/0327825 A1 | 11/2015 | Suzuki |
| 2015/0352376 A1 | 12/2015 | Wiggers |
| 2016/0067479 A1 | 3/2016 | Marcovecchio |
| 2016/0136460 A1 | 5/2016 | Baltes |
| 2016/0166857 A1 | 6/2016 | Nelms |
| 2016/0287906 A1 | 10/2016 | Nord |
| 2016/0310762 A1 | 10/2016 | Ramezanzadeh Moghadam |
| 2017/0021194 A1 | 1/2017 | Nelms |
| 2017/0173367 A1 | 6/2017 | Seuntjens |
| 2017/0177812 A1 | 6/2017 | Sjölund |
| 2017/0225015 A1* | 8/2017 | Thieme ............ A61B 6/5258 |
| 2017/0274225 A1 | 9/2017 | Baecklund |
| 2018/0028143 A1 | 2/2018 | Wiggers |
| 2018/0185672 A1 | 7/2018 | Ramezanzadeh Moghadam |
| 2018/0243586 A1 | 8/2018 | Ramezanzadeh Moghadam |
| 2018/0250529 A1 | 9/2018 | Seuntjens |
| 2018/0250531 A1* | 9/2018 | Ansorge ............ G01T 1/2914 |
| 2019/0298285 A1* | 10/2019 | Rakic ............... A61B 6/035 |
| 2020/0253001 A1 | 8/2020 | Nauditt |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2457237 | 5/2012 |
| EP | 2708919 A2 | 3/2014 |
| EP | 2865417 | 4/2015 |
| EP | 2904974 | 8/2015 |
| EP | 3074088 | 10/2016 |
| EP | 3075417 | 10/2016 |
| JP | 05154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 | 12/2013 |
| WO | 2015024360 | 2/2015 |
| WO | 2015073899 | 5/2015 |
| WO | 2016172352 | 10/2016 |
| WO | 2019157249 A | 8/2019 |

OTHER PUBLICATIONS

"Hi-Art,"; www.tomotherapy.com; TomoTherapy, Madison, WI; 2007; pp. 1-8.

"Rapid Arc"; Varian Medical Systems, Inc., Palo Alto, CA; www.varian.com; 2007; pp. 1-8.

"VMAT"; Elekta,Ltd., Crawley UK; Document No. 4513 3710770; Oct. 8, 2008, 8 pages.

"Waterphantom Dosimetry"; Medical Physics, vol. 3, May/Jun. 1976; pp. 189.

Ahnesjo et al. Phys. Med. Biol. 44, R99-R155 1999.

Ahnesjo et al., Acta. Oncol., 26, 49-56, 1987.

Ahnesjo, Med. Phys. 16, 577-92, 1989.

(56) References Cited

OTHER PUBLICATIONS

Albers et al., CRC Handbook of Chemistry and Physics, 87th Ed., Edited by R.C. Weast (CRC, Cleveland, 1976. pp. F-11, D-171, E-6. (4 pages).

Almond et al. In "AAPM TG-51 Protocol for Clinical Reference Dosimetry of Hign Energy Photon and Electron Beams" (Med. Phys. VI, 26, pp. 1847-1870, 1999.

Amanatides et al., Eurographics '87, Conference Proceedings, 1987, 10 pages.

Aspen Aerogels, Pyrogel.RTM. 2250 Datasheet (Aspen Aerogels, Inc., Northborough, 2010). 2 pages.

Benedick Fraass; "Quality Assurance for Clinical Radiotherapy Treatment Planning," Med Phys., 25(10), Oct. 1998; pp. 1773-1829.

Berlyand et al., "Portable Calorimeter for Measuring Absorbed Doses of X-Rays and Electrons from Accelerators", translated from Izeritel'naya Teknika, No. 11, Nov. 1991, pp. 56-58.

Boutillon in "Gap Correction for the Calorimetric Measurement of Absorbed Dose in Graphite with a 60Co Beam" (Phys. Med. Biol., vol. 34, pp. 1809-1821, 1989.

Brusasco, C, et al. 'A Dosimetry System for Fast Measurement of 3D Depth-dose Profiles in Charged-particle Tumor Therapy with Scanning Techniques.' Nuclear Instruments & Methods in Physics Research, Section—B: Beam Interactions With Materials and Atom 168.4 (2000): 578-92.

Cyberknife; Cyberknife Systems; "The Standard of Radiosurgery" by Accuracy, Sunnyvale, CA; 2009; pp. 1-6.

D.W.O. Rogers; "Montey Carlo Techniques in Radiotherapy,"; Physics in Canada, Medical Physics Special Issue, v. 58 #2; 2002; pp. 63-70.

Daures et al., "New Constant-Temperature Operating Mode for Graphite Calorimeter at LNE-LNHB", Physics in Medicine and Biology, vol. 50, 2005, No. pp. 4035-4052.

Daures et al., "Small section graphite calorimeter (CR10) at LNE-LNHB for measurement in small beams for IMRT", Metrologica, (Dec. 1, 2011), XP020229547, 5 pages.

Daures et al., "Small Section Graphite Calorimeter (GR-10) at LNE-LNHB for Measurements in Small Beams for IMRT Metrologia", vol. 49, No. 5, 2012, pp. S174-S178.

Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.

Domen, "Absorbed Dose Water Calorimeter" (Med. Phys., vol. 7, pp. 157-159).

Duane et al., "An Absorbed Dose Calorimeter for IMRT Dosimetry", Metrologia, vol. 49, No. 5, 2012, pp. S168-S173.

EP2277353 Search Report dated Jul. 21, 2017; 10 pages.

EP2237237 Supplemental European Search Report and Written Opinion dated Mar. 8, 2017; 10 pages.

G.J. Kutcher; "Comprehensive AQ for Radiation Oncology Report;" AAPM Radiation Therapy Committee Task Group 40; Med. Phys., 21; Apr. 1994; pp. 581-618.

Iaea, Trs., "398. Absorbed Dose Determination in External Beam Radiotherapy: An International Code of Practice for Dosimetry based on Standards of Absorbed Dose to Water," Vienna International Atomic Energy Agency (2000). 242 pages.

Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.

J. Seuntjens and S. Duane, "Photon absorbed dose standards," Metrologia 46, S39-S58 (2009).

Joseph O. Deasy; "A Computational Environment for Radiotherapy Research," Med. Phys. 30, (5), May 2003; pp. 979-985.

Kawrakow et al. In "The EGSnrc Code System: Monte-Carlo Simulation of Electron and Photon Transport" (Canadian National Research Center, NRC Report PIRS-701, 2006.

Linacre, J.K. , "Harwell Graphite Calorimeter", IAEA, vol. 47, 1970 (pp. 46-54.).

Liu et al., Med. Phys. 24, 1729-1741, 1997.

Lu et al., Phys. Med. Biol. 50, 655-680, 2005.

Mackie et al., "Generation of Photon Energy Deposition Kernels Using the EGS Monte Carlo Code," 1988, Phys. Med. Biol. 33, pp. 1-20.

Mackie et al., Med. Phys. 12, 188-196, 1985.

Mackie et al., Proceedings of the 1996 AAPM Summer School, 1996. 36 pages.

Mackie et al., Use of Comp. In Rad. Ther., 107-110 1987.

MapCALC; www.sunnuclear.com; manufactured by Sun Nuclear Corp.; Melbourne, FL; 2009, 2 pages.

MapCheck and EPIDose; www.sunnuclear.com; manufactured by Sun Nuclear Corp.; Melbourne,FL; 2010, 8 pages.

Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 82(2); Feb. 2007; pp. 201-201.

McEwen at al., 'A Portable Calorimeter for Measuring Absorbed Dose in the Radiotherapy Clinic', Physics in Medicine and Biology, vol. 45, No. 12, Dec. 2000, pp. 3675-3691.

McDermott et al.; "Replacing Pretreatment Verification with In Vivo EPID Dosimetry for Prostate IMRT"; International Journal of Radiation: Oncology Biology Physics, Pergamon Press, USA, vol. 67, No. 5, Mar. 28, 2007, pp. 1568-1577, XP022101268, ISSN: 0360-3016, DOI: 10.1016/J.IJROBP.2006.11.047.

McDonald et al., "Portable Tissue Equivalent Calorimeter", Medical Physics, vol. 3, 2, Mar.-Apr. 1976, pp. 80-86.

McEwen et al., Portable Graphite Calorimeter for Measuring Absorbed Dose in the Radiotherapy Clinic.Standards and Codes of Practice in Medical Radiation Dosimetry,IAEA-CN-96-9P,2002, pp. 115-121.

McEwen et al.; "A portable calorimeter for measuring absorbed dose in radiotherapy clinic"; Dec. 2000; Phys. Med. Biol., vol. 45; pp. 3675-3691.

Miller, "Polystyrene Calorimeter for Electron Beam Dose Measurements", Radiation Physics Chemistry vol. 46, No. 4-6, Aug. 1995, pp. 1243-1246.

Mohan et al., Med. Phys. 12, 592-597, 1985.

Myers et al., "Precision Adiabatic Gamma-Ray Calorimeter using Thermistor Thermometry", Review of Scientific Instruments, vol. 32, No. 9, Sep. 1961, pp. 1013-1015.

Nelms, Benjamin et al.; "Evalution of a Fast Method of EPID-based Dosimetry for Intensity-modulated Radiation Therapy"; Journal of Applied Clinical Medical Physics, Jan. 1, 2010, pp. 140-157, XP055476020.

Nelms, Benjamin. "Variation in External Beam Treatment, Plan Quality: An Inter-institutional Study of Planners and Planning Systems." Practical Radiation Oncology 2.4 (2012): 296-305.

Nutbrown et. "Evaluation of Factors to Convert Absorbed Dose Calibrations in Graphite to Water for Mega-Voltage Photon Beams" (UK National Pysical Laboratory, NPL Report CIRM 37, 2000. 45 pages.

Ostrowsky et al., "The Construction of the Graphite Calorimeter GR9 at LNE-LNHB (Geometrical and technical considerations)", Report CEA-R-6184, 2008, 52 pages.

Otto, Med. Phys. 35, 310-317, 2008.

Owen et al "Correction for the Effect of the Gaps around the Core of an Absorbed Dose Graphite Calorimeter in High Energy Photon Radiation" (Phys. Med. Biol., vol. 36, pp. 1699-1704, 1991.

Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.

Papanikolaou et al., Med. Phys. 20, 1327-1336, 1993.

PCT App. No. PCT/US2009/036775; International Preliminary Report on Patentability Chapter II and Written Opinion dated Sep. 12, 2010; 12 pages.

PCT App. No. PCT/US2009/036775; International Search Report dated Nov. 12, 2009; 2 pages.

PCT App. No. PCT/US2009/036917; International Preliminary Report on Chapter II Patentability dated Mar. 15, 2011. 3 pages.

PCT App. No. PCT/US2009/036917; International Search Report dated Sep. 17, 2009. 2 pages.

(56) References Cited

OTHER PUBLICATIONS

PCT App. No. PCT/US2009/036917; Written Opinion dated Sep. 12, 2010; 4 pages.
PCT App. No. PCT/US2009/043341; International Preliminary Report on Patentability Chapter I dated Nov. 9, 2010. 4 pages.
PCT App. No. PCT/US2009/043341; International Search Report dated Jan. 5, 2010. 3 pages.
PCT App. No. PCT/US2009/043341; Written Opinion of the International Search Authority dated Nov. 8, 2010. 3 pages.
PCT App. No. PCT/US2010/042680; International Preliminary Report on Patentability Chapter I dated Jan. 24, 2012; 9 pages.
PCT App. No. PCT/US2010/042680; International Search Report dated Jan. 27, 2011; 2 pages.
PCT App. No. PCT/US2010/042680; International Written Opinion dated Jan. 23, 2012; 8 pages.
PCT App. No. PCT/US2012/053440; International Preliminary Report on Patentability Chapter I dated Mar. 3, 2015; 8 pages.
PCT App. No. PCT/US2012/053440; International Search Report and Written Opinion dated Mar. 26, 2014; 3 pages.
PCT App. No. PCT/US2012/058345; International Preliminary Report on Patentability Chapter I dated Apr. 1, 2014; 5 pages.
PCT App. No. PCT/US2012/058345; International Search Report dated Apr. 17, 2013; 3 pages.
PCT App. No. PCT/US2012/058345; International Written Opinion of the International Search Authority dated Mar. 29, 2014; 4 pages.
PCT App. No. PCT/US2014/065808; International Preliminary Report on Patentability Chapter I dated May 17, 2016; 7 pages.
PCT App. No. PCT/US2014/065808; International Search Report and Written Opinion dated May 21, 2015; 9 pages.
PCT App. No. PCT/US2015/024360; International Preliminary Report on Patentability Chapter I dated Oct. 4, 2016; 9 pages.
PCT App. No. PCT/US2015/024360; International Search Report and Written Opinion dated Oct. 8, 2015; 13 page.
PCT App. No. PCT/US2016/028664; International Preliminary Report on Patentability dated Nov. 2, 2017; 5 pages.
PCT App. No. PCT/US2017/062608; International Search Report and Written Opinion dated Feb. 22, 2018; 11 pages.
PCT App. No. PCT/US2018/020320; International Preliminary Report on Patentability Chapter I dated Sep. 12, 2019. pp. 1-11.
PCT App. No. PCT/US2018/020320; International Search Report and Written Opinion dated Jul. 24, 2018; 18 pages.
PCT/US2017/044472; International Search Report and Written Opinion of the International Searching Authority, or the Declaration dated Oct. 13, 17; 12 pages.
Petree et al., "A Comparison of Absorbed Dose Determinations in Graphite by Cavity Ionization Measurements and by Calorimetry", Journal of Research of the National Bureau of Standards—C. Engineering and Instrumentation, vol. 71 C, No. 1, Jan.-Mar. 1967, pp. 19-27.
Picard et al., "Construction of an Absorbed-Dose Graphite Calorimeter", Report BIPM-09/01' May 2009, 12 pages.
R. Alfonso et al., 'A new formalism for reference dosimetry of small and nonstandard fields,' Med. Phys. 35, 5179-5186 (2008).
Renaud et al., "Development of a graphite probe calorimeter for absolute clinical dosimetry", Med. Phvs., (Jan. 9, 2013), vol. 40, No. 2, p. 020701, XP012170941.
Robert M. Eisberg; "Fundamentals of Modern Physics," Chapter 9—Perturbation Theory; John Wiley & Sons; 1967; pp. 268-272.
Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.
Ross et al. In "Water Calorimetry for Radiation Dosimetry" (Phys. Med. Biol., vol. 41, pp. I-29).
S. Picard, D. T. Burns, and P. Roger, "Determination of the specific heat capacity of a graphite sample using absolute and differential methods," Metrologia 44, 294-302 (2007).
Sander et al., "NPL's new absorbed dose standard for the calibration of HDR 192Ir brachytherapy sources," Metrologia 49, S184-S188 (2012).
Seuntjens et al., Review of Calorimeter Based Absorbed Dose to Water Standards, Standards and Codes of Practice in Medical Radiation Dosimetry, IAEA-CN-96-3,2002 p. 37-66.
Stewart in "The Development of New Devices for Accurate Radiation Dose Measurement: A garded Liquid Ionization Chamber and an Electron Sealed Water Calorimeter" (Ph. D. Dissertation McGill University, 2007.
Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.
T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Williams, SIGGRAPH Comput. Graph. 17, 3, 1-11, 1983.
Witzani et al., "A Graphite Absorbed-Dose Calorimeter in the Quasi-Isothermal Mode of Operation", Metrologia, vol. 20, No. 3, 1984, pp. 73-79.
Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).
Yan et al., Phys. Med. Biol. 42, 123-132, 1997.
Yu, Phys. Med. Biol. 40, 1435-1449, 1995.

\* cited by examiner

SYSTEMS AND METHODS TO ACCOUNT FOR TILT OF A RADIATION MEASUREMENT SYSTEM

RELATED APPLICATION(S)

This application claims priority to and the benefit of U.S. Provisional Application No. 62/738,613, filed Sep. 28, 2018, titled "Systems and Methods to Account for Tilt of a Radiation Measurement System," which is hereby incorporated by reference.

BACKGROUND

Calibration of radiation delivery systems is needed to ensure proper delivery of radiotherapy. Radiation delivery profiles may be measured using a phantom to approximate the absorption of radiation by a patient. With measurement of what radiation a delivery system actually delivers (e.g., to the phantom), the radiation delivery system can be adjusted or calibrated for optimal delivery of a prescribed dose to a patient.

SUMMARY

Systems, methods, and computer program products that are configured to account for tilt of a radiation measurement system are disclosed. In one aspect, a system includes a scanning system including a radiation detector, the scanning system configured to enable movement of the radiation detector. The system also includes at least one programmable processor and a non-transitory machine-readable medium storing instructions which, when executed by the at least one programmable processor, cause the at least one programmable processor to perform various operations. The operations include moving the radiation detector through a first vertical calibration path and recording a first radiation detector response within 3 cm of a water surface, moving the radiation detector through a second vertical calibration path and recording a second radiation detector response within 3 cm of the water surface, moving the radiation detector through a third vertical calibration path and recording a third radiation detector response within 3 cm of the water surface, and controlling the scanning system to move the radiation detector through at least one measurement path that takes into account a scanning system tilt, the at least one measurement path determined based on at least the first, second, and third radiation detector responses.

In an interrelated aspect, a system includes a scanning system including multiple radiation detectors, the scanning system configured to enable movement of the radiation detectors. The system also includes at least one programmable processor and a non-transitory machine-readable medium storing instructions which, when executed by the at least one programmable processor, cause the at least one programmable processor to perform various operations. The operations include moving the multiple radiation detectors through multiple calibration paths and recording multiple radiation detector responses within 3 cm of a water surface, and controlling the scanning system to move a radiation detector through at least one measurement path that takes into account a scanning system tilt, the at least one measurement path determined based on at least the multiple radiation detector responses.

In yet another interrelated aspect, a system includes a scanning system including multiple radiation detectors, the scanning system configured to enable movement of the radiation detectors. The system also includes at least one programmable processor and a non-transitory machine-readable medium storing instructions which, when executed by the at least one programmable processor, cause the at least one programmable processor to perform various operations. The operations include moving the radiation detector through a first vertical calibration path and recording a first radiation detector response within 3 cm of a water surface, moving the radiation detector through a second vertical calibration path and recording a second radiation detector response within 3 cm of the water surface, moving the radiation detector through a third vertical calibration path and recording a third radiation detector response within 3 cm of the water surface, and controlling an actuator to cause a leveling of the scanning system such that at least one movement axis of the scanning system is parallel to the water surface, the controlling based on at least the first, second, and third radiation detector responses.

In another interrelated aspect, a computer program product includes a non-transitory, machine-readable medium storing instructions which, when executed by at least one programmable processor, cause the at least one programmable processor to perform various operations. The operations include moving a radiation detector through a first vertical calibration path and recording a first radiation detector response within 3 cm of a water surface, moving the radiation detector through a second vertical calibration path and recording a second radiation detector response within 3 cm of the water surface, moving the radiation detector through a third vertical calibration path and recording a third radiation detector response within 3 cm of the water surface, and controlling a scanning system to move the radiation detector through at least one measurement path that takes into account a scanning system tilt, the at least one measurement path determined based on at least the first, second, and third radiation detector responses.

In some variations, the measurement path determination can be based on high-gradient regions of the first, second, and third radiation detector responses.

In other variations, the operations can further include calculating an offset based on any two of the first radiation detector response, the second radiation detector response, and the third radiation detector response. The measurement path determination can be based on at least the offset. The offset can be calculated in a high-gradient region of the first, second, or third radiation detector responses.

In yet other variations, the operations can further include performing functional fits to the any two radiation detector responses, calculating feature locations based on at least the functional fits, and determining the offset based on differences in the any two radiation detector responses at the feature locations. The feature locations can correspond to at least one of a maximum gradient location, an inflection point, a maximum curvature, and a specific dose value.

In some variations, the operations can further include calculating, based on at least the offset, a normal vector representing a plane of the scanning system or calculating, based on at least the offset, a pair of angles representing the plane of the scanning system. The measurement path determination can be based on at least the normal vector or the pair of angles.

In one aspect, a computer program product includes a non-transitory, machine-readable medium storing instructions which, when executed by at least one programmable processor, cause the at least one programmable processor to perform operations including moving a radiation detector through a first vertical calibration path and recording a first radiation detector response within 3 cm of a water surface, moving the radiation detector through a second vertical calibration path and recording a second radiation detector response within 3 cm of the water surface, moving the radiation detector through a third vertical calibration path and recording a third radiation detector response within 3 cm of the water surface, calculating a correction function based on at least the first, second, and third radiation detector responses, controlling the scanning system to move the radiation detector through a raw data path and recording, during the movement of the radiation detector along the raw data path, a raw data radiation detector response, and providing a corrected radiation detector response based on at least an application of the correction function to the raw data radiation detector response.

In an interrelated aspect, a computer program product includes a non-transitory, machine-readable medium storing instructions which, when executed by at least one programmable processor, cause the at least one programmable processor to perform operations including moving multiple radiation detectors through multiple calibration paths and recording multiple radiation detector responses within 3 cm of a water surface, and controlling a scanning system to move a radiation detector through at least one measurement path that takes into account a scanning system tilt, the at least one measurement path determined based on at least the multiple radiation detector responses.

In an interrelated aspect, a computer program product includes a non-transitory, machine-readable medium storing instructions which, when executed by at least one programmable processor, cause the at least one programmable processor to perform operations including moving a radiation detector through a first vertical calibration path and recording a first radiation detector response within 3 cm of a water surface, moving the radiation detector through a second vertical calibration path and recording a second radiation detector response within 3 cm of the water surface, moving the radiation detector through a third vertical calibration path and recording a third radiation detector response within 3 cm of the water surface, and controlling an actuator to cause a leveling of a scanning system such that at least one movement axis of the scanning system is parallel to the water surface, the controlling based on at least the first, second, and third radiation detector responses.

In some variations, the operations can further include calculating an offset based on any two of the first radiation detector response, the second radiation detector response, and the third radiation detector response, where the controlling of the actuator to cause the leveling of the scanning system can be further based on the offset.

Embodiments of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more embodiments of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular embodiments, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings.

DETAILED DESCRIPTION

Radiation delivery systems can be used, for example, for delivering radiation therapy to patients. Radiation delivery systems can include, for example, linear accelerators, radio-isotope systems (e.g., cobalt sources). The amount and location of radiation delivered can be specified by a radiation treatment plan, which can include specific instructions for how and under what configuration a radiation delivery system is to be operated. Before or between radiation therapy treatments, the radiation delivery system can be calibrated to ensure that the radiation is delivered as intended. These calibrations can include characterizing the radiation beam (e.g., fluence, homogeneity, energy, etc.). As part of such calibrations, a phantom can be used to provide a volume that can receive radiation. Phantoms can be, for example, water phantoms, solid water phantoms or water-equivalent phantoms. The phantoms can be circular (cylindrical), rectangular, or anthropomorphic-shaped. Radiation detectors can be used in or around the phantom to measure a delivered radiation dose for comparison with expected radiation output. Accordingly, the systems, computer program products, and methods described herein provide embodiments that can, among other things, enable accurate measurements of radiation even in the case where the phantom is misaligned or tilted relative to the radiation beam. Such embodiments can include using the radiation detector itself to determine the misalignment, without having to locate a water surface.

Figure 1:
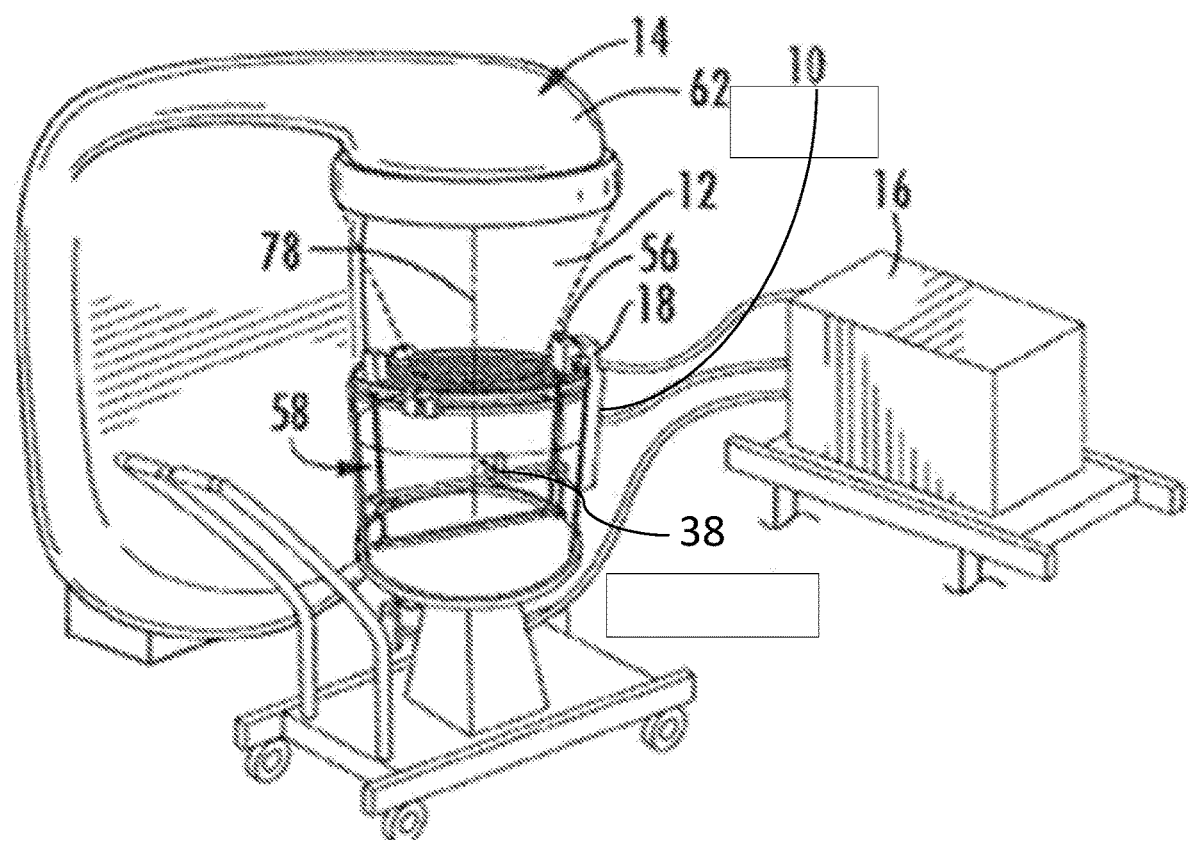
FIG. 1 is a simplified diagram of an exemplary radiation source and exemplary phantom and radiation detection scanning system.
Figure 2:
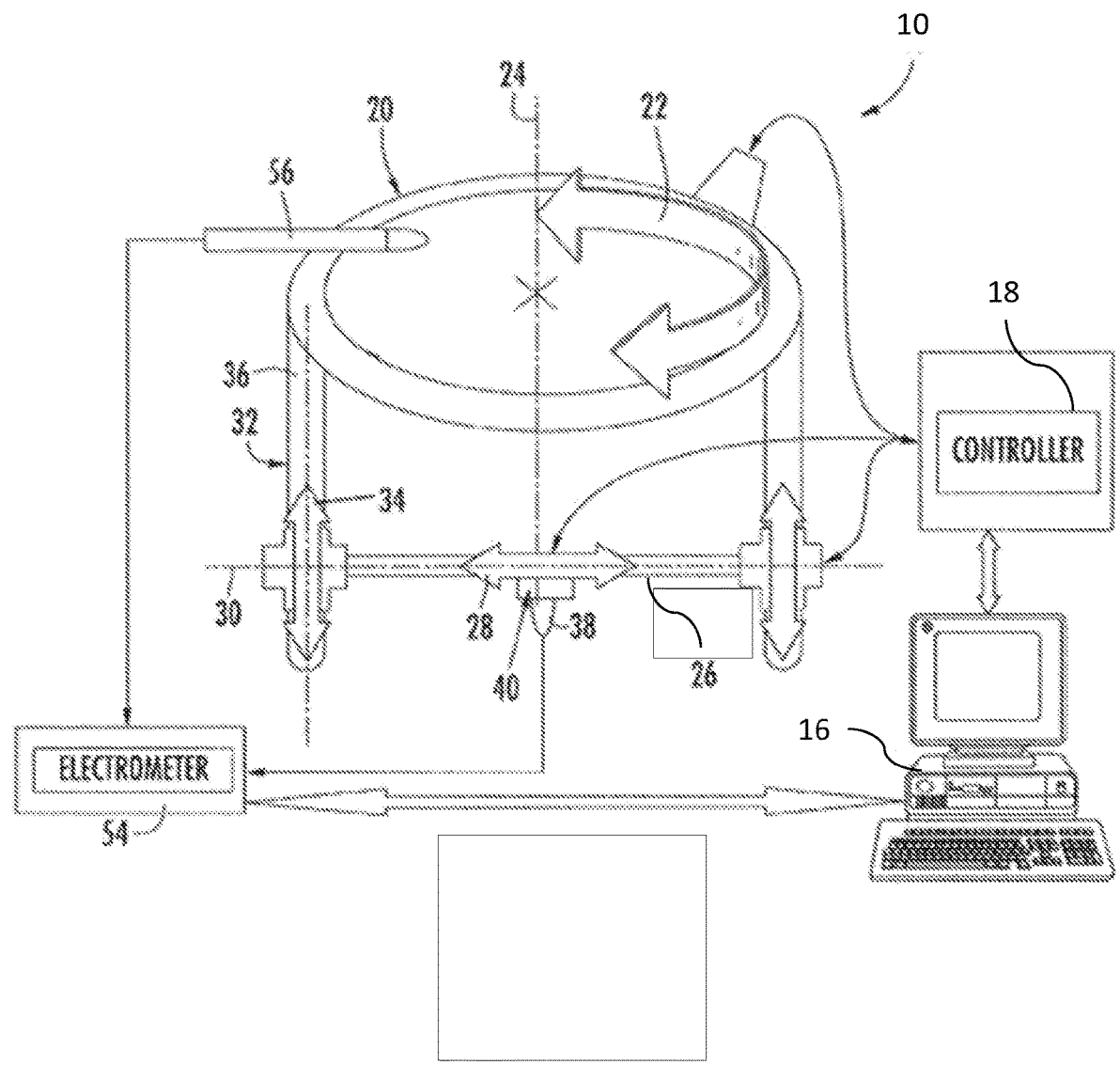
FIG. 2 is a detailed diagram of an exemplary scanning system, in accordance with certain aspects of the present disclosure.

FIG. 1 is a simplified diagram of an exemplary radiation source 14 and exemplary scanning system 10 with a radiation detector 38, in accordance with certain aspects of the present disclosure. FIG. 2 is a detailed diagram of the exemplary scanning system 10, in accordance with certain aspects of the present disclosure.

Radiation detector 38 can be provided for measuring radiation 12 emitted from radiation source 14, for example along central axis 78. Types of radiation detectors can include, for example, gaseous ionization detectors, ionization chambers, proportional counters, scintillation counters, semiconductor detectors, dosimeters (e.g. films), or electroscopes or electrometers. As illustrated in FIG. 1, scanning system 10 can include radiation detector 38 and can be configured to enable movement of radiation detector 38 inside phantom 58. To effect movement of radiation detector 38, scanning system 10 can include any combination of drives, including, for example, linear drives, ring drives, diameter drives, vertical drives, horizontal drives, etc. Scanning system 10 can also include tracks, belts, gears, motors, or the like to allow positioning of radiation detector 38. Scanning system 10 can also be connected to a processor 16 having analysis and data storage capabilities and controller 18 operable with the processor.

With reference to the exemplary system depicted in FIG. 2, ring drive 20 can be operable with controller 18 for providing a rotational movement 22 about first axis 24 responsive to commands from the controller. Horizontal drive 26 can be operable with controller 18 for providing horizontal movement 28 along second axis 30. By way of example, horizontal drive 26 can be operable with ring drive 20 for providing rotational movement 22. Vertical drive 32 can be operable with controller 18 for providing vertical movement 34 of horizontal drive 26 along third axis 36 responsive to commands from controller 18. Radiation detector 38 can be carried by mount 40 affixed to horizontal drive 26 for locating it along horizontal drive 26 by horizontal movement 28. Radiation detector 38 can provide sensing signals to processor 16 for selected locations of the radiation detector when orientated through the circular (rotational), horizontal, and vertical movements 22, 28, 34 along the first, second and third axes 24, 30, 36, respectively, as a result of commands from controller 18. As used herein, the term "drive" refers to motors, tracks, belts, bearings, etc., that enable the desired motion associated with the drive (e.g., horizontal, vertical, rotational).

With reference again to FIG. 2, scanning system 10 can include electrometer 54 operable between processor 16 and radiation detector 38. In addition, a reference detector 56 can be located at a fixed location for comparing the sensing signals from the radiation detector 38 to the reference detector 56. As illustrated with reference again to FIG. 1, a cylindrical water tank 58 carrying water (one example of a "phantom") can be dimensioned for movement of the radiation detector 38 and drives 20, 26, 32 described above. While a circular cross-section water phantom 58 is shown, the technologies of the present disclosure are contemplated to be applicable to other shapes and types of phantoms, for example, square, rectangular, hexagonal, etc. Controller 18 can be capable of communicating movement commands and receiving encoder information from the motors and bi-directional communication of movement command and encoder position data to programmable processor 16.

The embodiment described herein is by way of example only for application to a cylindrical phantom/scanning system. However, other geometrically shaped vessels (e.g., square, rectangular) may be employed without compromising the benefits of the scanning system 10. The scanning system can be a Cartesian scanning system where instead of ring drive 20, there can be two horizontal drives (e.g. corresponding to an X axis and a Y axis), which, when combined with vertical drive 32, can also provide three-dimensional movement of radiation detector 38.

During scans, the phantom/vessel may contain water, or air scans can be performed with an empty vessel. Scanning system 10 may also be implemented without a vessel and assembled in a self-supporting frame that rests on a treatment couch, or may be mounted to the head of radiation source 14 for testing radiation beam characteristics as gantry 62 is moved.

Figure 3:
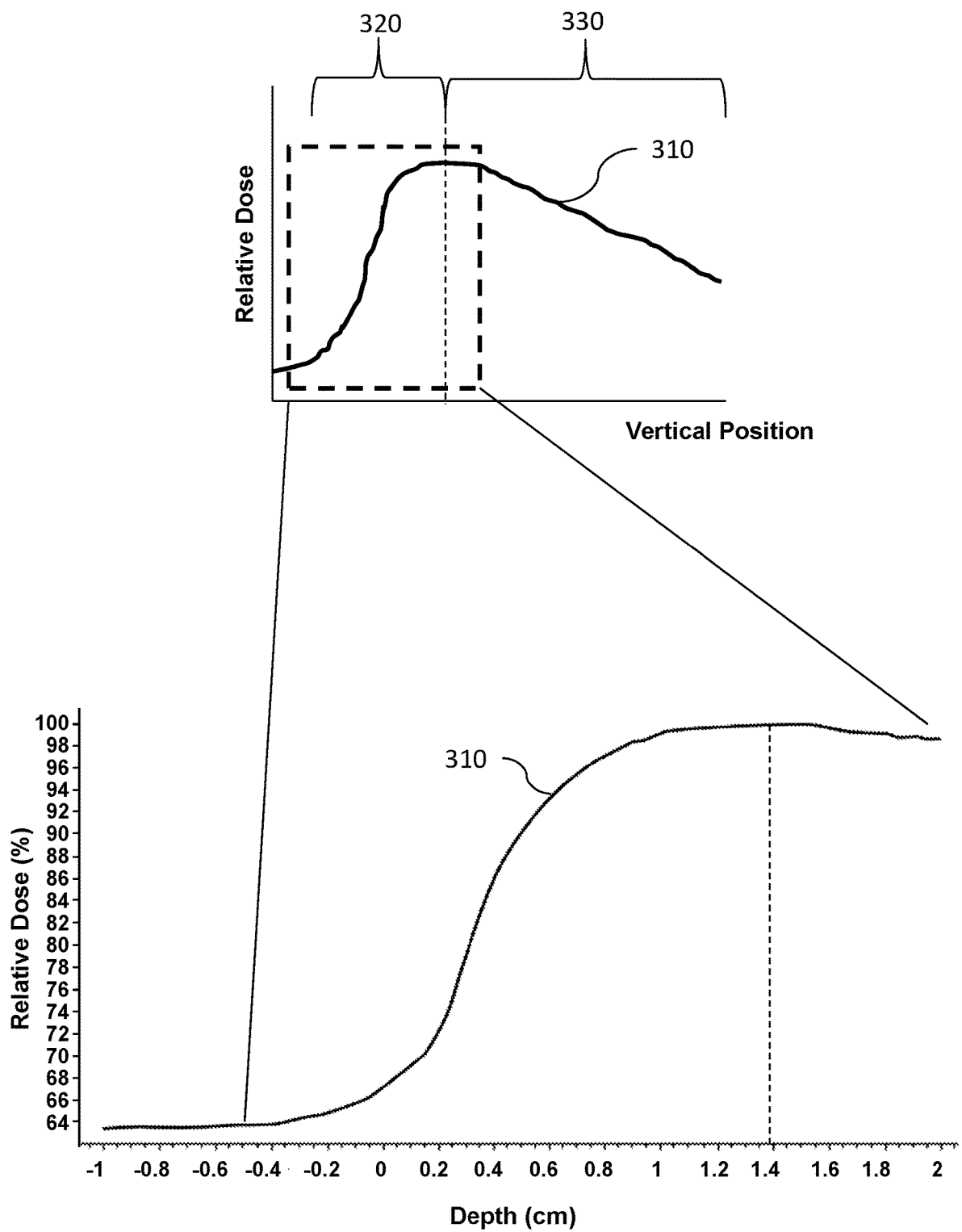
FIG. 3 is a simplified diagram of a profile of dose delivery in a phantom vs. vertical position of a radiation detector, in accordance with certain aspects of the present disclosure.

FIG. 3 is a simplified diagram of a profile of dose delivery in a phantom vs. vertical position of a radiation detector, in accordance with certain aspects of the present disclosure.

During a calibration, scanning system 10 can be used with a phantom that provides a generally known absorption of radiation. The dose delivered to the phantom varies with depth because the radiation beam is attenuated, absorbed and scattered as it passes through the material of the phantom. Also, the measured dose can vary near the edge of the phantom, as further described below. As used herein, the term "dose" means the deposition of energy in a material as a result of exposure to ionizing radiation. It is understood that when referring to the interaction of radiation with a phantom (e.g., a water phantom, solid water phantom, or any other absorber), that the "dose" refers to the material of the phantom (e.g., water, solid water, etc.). As the dose can be determined based on data from radiation detector 38, or any other sort of radiation detector, the illustrated dose curves herein are generally described as the "radiation detector response." As used herein, the term "radiation detector response" means any response to radiation of radiation detector 38 (or other types of radiation detectors described herein), but can also refer to a response of radiation detector 38 converted to dose, relative dose, etc.

The top panel of FIG. 3 illustrates an example of dose 310 as measured at different positions in phantom 58. In many example plots shown herein, the dose is shown as normalized to 100% at the peak of the measured dose and described as "relative dose." Accordingly, as used herein, when referring to "dose" this can also refer, for simplicity, to "relative dose." As illustrated in the top panel, the dose builds up to a maximum and then falls off further into the phantom 58. This introduces two regions of the radiation detector response.

The first region is the "high-gradient region" 320, where scattered radiation (electrons and photons) from the primary radiation is not in equilibrium as a function of primary fluence per unit path length. Equilibrium occurs at a depth that is dependent on the primary radiation energy and field size. Equilibrium depths typically range from 0.1 to 5 cm, where equilibrium depth increases with beam energy, due primarily to the extended range of the secondary radiation. As depth increases, so too does the detector response to the increasing scattered radiation. The rate of increase in the detector response with depth continues until equilibrium is reached. At this depth, the detector response has peaked, and the scattered radiation is in equilibrium with the primary radiation fluence which then decreases by primary attenuation with increasing depth. After the peak, the detector response decreases along with primary radiation attenuation in the phantom. The rate of increase in the detector response before the peak is greater than the rate of decrease after the peak, hence the "high-gradient region."

The second region 330 is where the delivered dose is directly relatable to the fluence of the radiation beam where, in any volume, as many electrons are stopped as set in motion. For discussion purposes only, as used herein, it will be assumed that the termination of the high-gradient region (illustrated by the vertical dashed line) is the location where the relative dose is a maximum. However, it should be understood that such a division is merely assumed for ease of discussion and that these processes occur on a continuum, and thus such a distinction should not be considered as overly limiting.

The inset indicated by the dashed square in the top panel of FIG. 3 is illustrated in the example of the bottom panel in FIG. 3. This provides an exemplary illustration of the relative dose in the high-gradient region as a function of vertical position of radiation detector 38 in phantom 58. Here, it can be seen that at some positions (e.g., between 0.2 cm and 0.6 cm), there can be a large gradient in relative dose. It is understood that the values shown with respect to relative dose and vertical position are examples only and that other curves corresponding to relative dose versus vertical position may be obtained. Similarly, the high-gradient region may not have the exact shape shown in the examples provided herein, as the specific radiation detector responses can be a function of beam energy, geometry, etc. The bottom panel in FIG. 3 is intended to merely illustrate one example where a high gradient region can occur close to top of phantom 58 (e.g., a water surface when phantom 58 is a water phantom 58).

Figure 4:
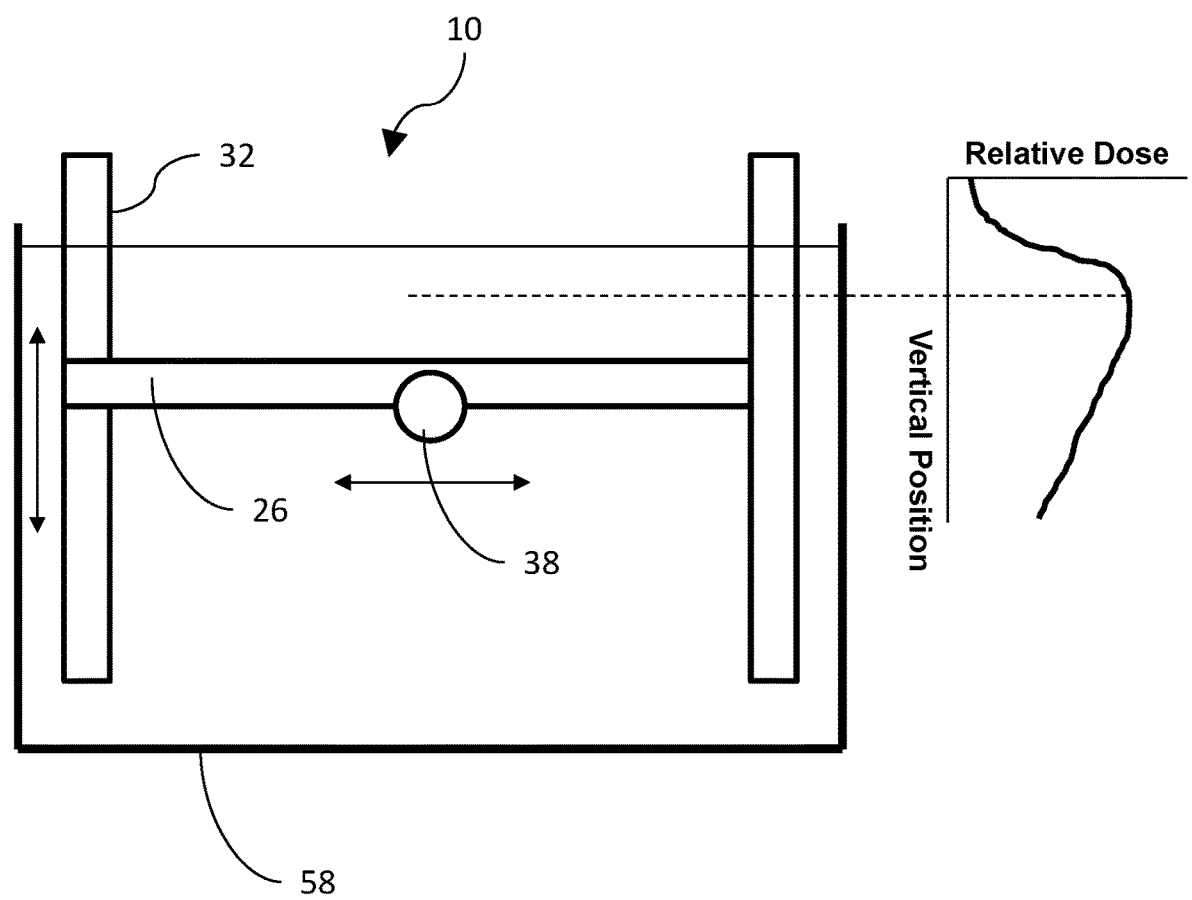
FIG. 4 is a simplified diagram illustrating an example of a level scanning system and phantom, in accordance with certain aspects of the present disclosure.

FIG. 4 is a simplified diagram illustrating an example of a level scanning system 10 and phantom 58, in accordance with certain aspects of the present disclosure.

As previously described, the measurement of dose can be a function of vertical position of radiation detector 38 in phantom 58. The simplified diagram of FIG. 4 shows a radiation detector that can be moved, for example, by a combination of a vertical drive and a horizontal drive.

The plot to the right of scanning system 10 illustrates conceptually how an example measurement of relative dose versus vertical position (also referred to herein as "radiation detector response") relates to scanning system 10 and phantom 58. As presented in FIG. 4, because scanning system 10 is level, a vertical scan of radiation detector at any location in phantom 58 will result in the same radiation detector response (under the simplifying assumption that the beam fluence is uniform or homogenous).

Figure 5:
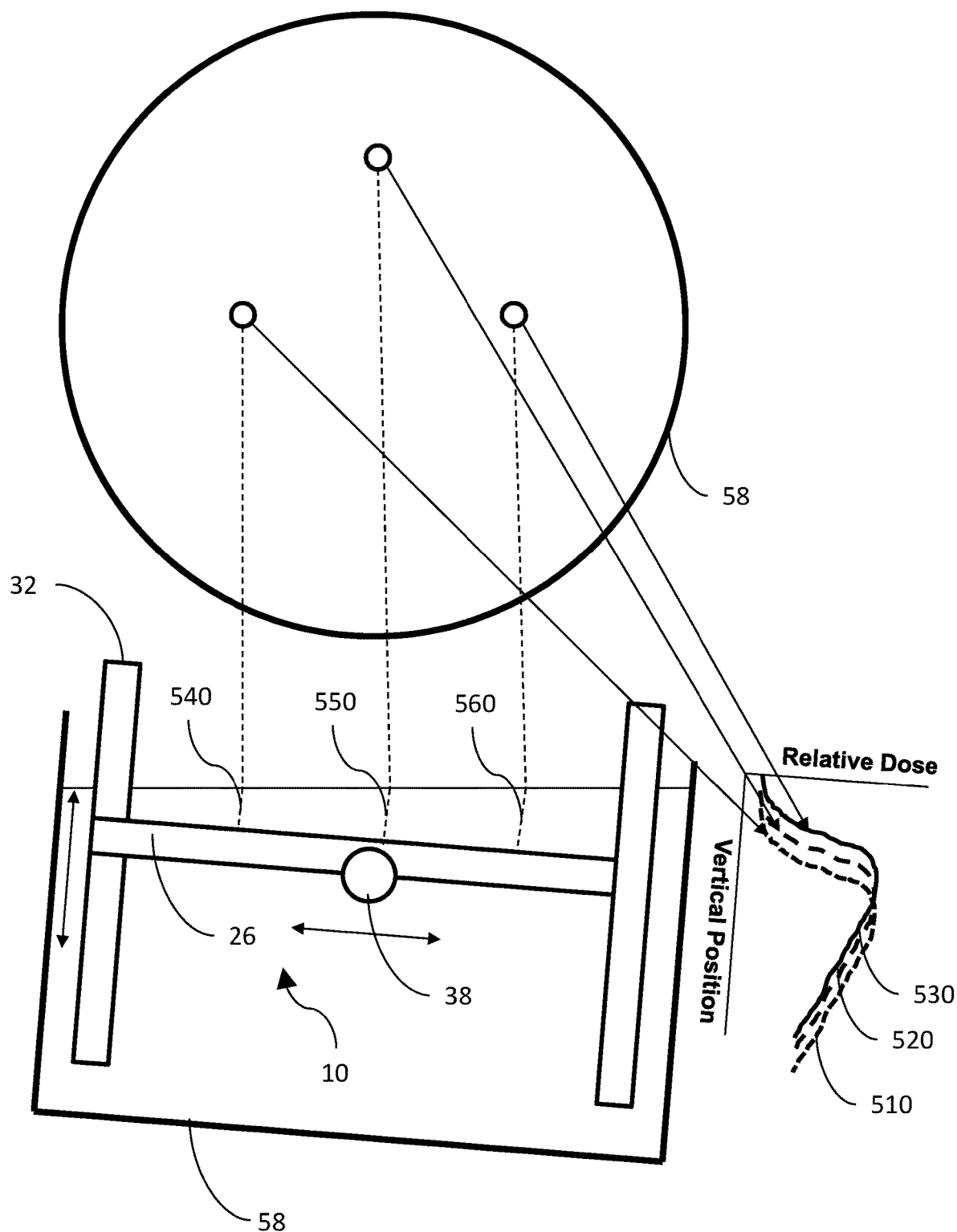
FIG. 5 is a simplified diagram illustrating an example of a tilted scanning system and phantom, in accordance with certain aspects of the present disclosure.

FIG. 5 is a simplified diagram illustrating an example of a tilted scanning system 10 and phantom 58, in accordance with certain aspects of the present disclosure.

Ideally, scanning system 10 and/or phantom 58 are "level" relative to the radiation beam (e.g., movement of the vertical drive is parallel to the central axis of the radiation beam and movement by the horizontal drives or ring drives is orthogonal to the central axis of the radiation beam). When scanning system 10 is tilted, the radiation detector response will be different when measured at different locations. A simplified illustration of this effect is shown by the example plot to the right of the tilted scanning system 10.

In the exemplary plot of FIG. 5, three radiation detector responses (510, 520, 530) are shown for three vertical scans (540, 550, 560) (also referred to herein as vertical calibration paths) performed by the vertical drive. Examples of three locations, as projected onto a water surface, are shown in the top portion of FIG. 5. Due to the scanning system tilt, the radiation detector responses plotted, as a function of vertical position, are offset from each other. Certain embodiments of the present disclosure can utilize measurements/calculations of these offsets to determine and compensate for scanning system tilt. Accordingly, disclosed herein are a number of different embodiments of systems, methods, and computer programs that allow for the physical and/or electronic correction of the effects of a tilted scanning system 10.

As discussed herein, it is generally assumed that a phantom vessel (e.g., a water tank) is aligned with the scanning system 10 such that when the vessel is tilted, the scanning system 10 is also tilted. However, this need not be the case. For example, it is contemplated that only the scanning system 10 may be tilted and that the phantom 58 is not tilted. Similarly, the scanning system 10 and the water tank can be separately tilted at different angles. In the present disclosure, when describing "tilt" or other equivalent expressions, this refers to the tilt of a scanning system 10 with respect to a water surface (or other such assumed horizontal surface of a phantom 58 that is taken to be perpendicular to a central axis of the radiation beam).

Furthermore, as used herein, when reference is made to "perpendicular," "orthogonal," "parallel," "level," "collinear," "coplanar," and other similar geometrical terms, it is understood that these are intended to include substantial approximations to the idealized definitions of such.

Figure 6:
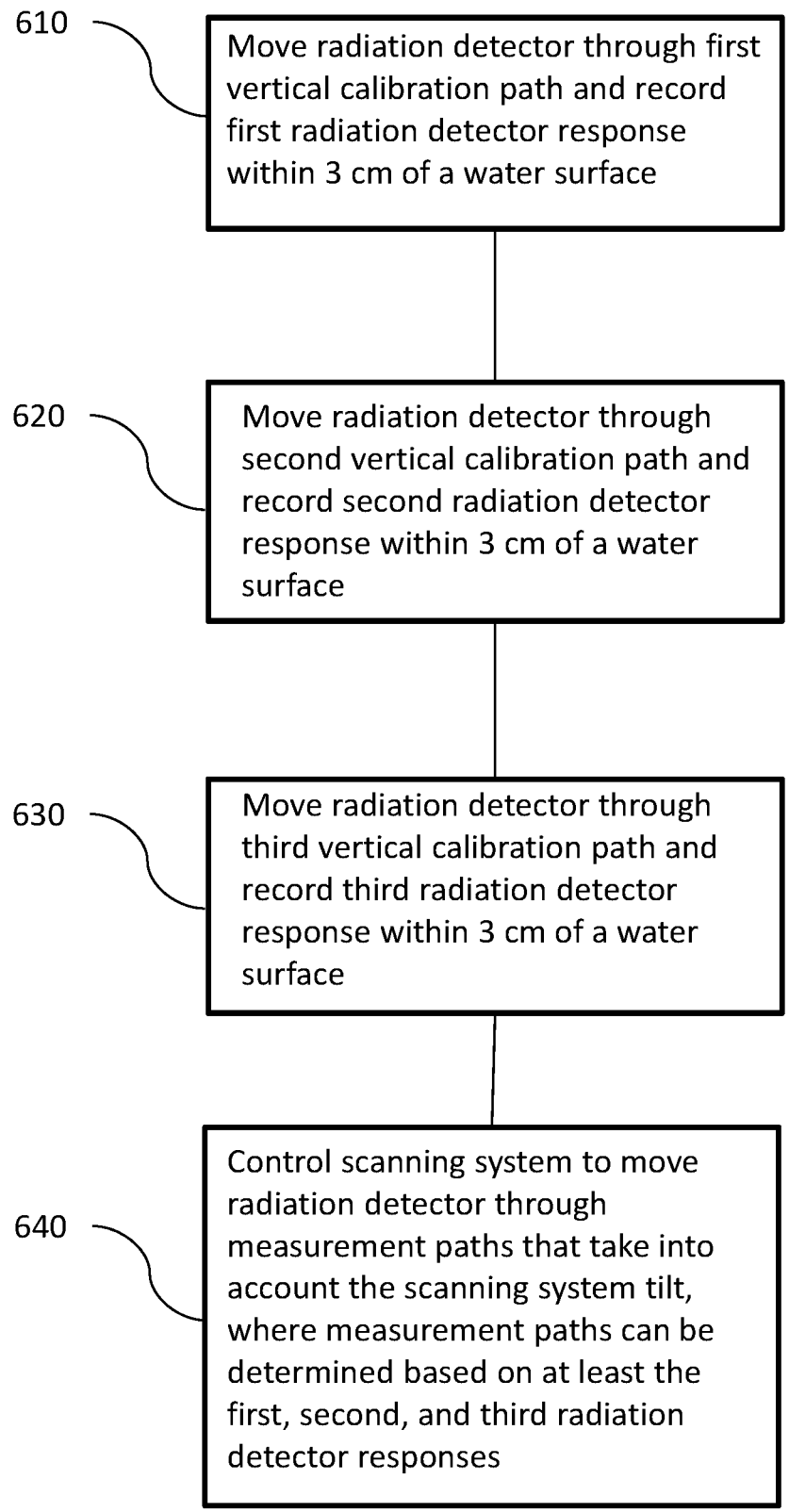
FIG. 6 is a process flow diagram describing an exemplary process for using a radiation detector to determine a scanning system tilt, in accordance with certain aspects of the present disclosure.

FIG. 6 is a process flow diagram describing exemplary process for using a single radiation detector to determine a scanning system tilt, in accordance with certain aspects of the present disclosure.

Radiation detector responses recorded along the three different paths, as shown, for example, in FIG. 5, can allow determination of the tilt of scanning system 10. In one embodiment, this can be done by a single radiation detector that is controlled to move vertically along three non-coplanar calibration paths. For example, at 610, a radiation detector can be moved through a first vertical calibration path and a first radiation detector response can be recorded, for example, within 3 cm of a water surface. As used herein, when referring to recording a radiation detector response within a certain distance of the water surface, it is understood that this means that the recording is done in or under the water surface. However, this does not preclude implementations where a measurement or calibration path may extend through or above a water surface. Also, at 620, a radiation detector can be moved through a second vertical calibration path and a second radiation detector response can be recorded, for example, within 3 cm of the water surface. Further, at 630, a radiation detector can be moved through a third vertical calibration path and a third radiation detector response can be recorded, for example, within 3 cm of the water surface. Though 3 cm is an example of where the high-gradient region can allow easier distinction between differences or offsets in radiation detector responses, measurements at other locations or in other regions can also be performed. It should be understood that 3 cm is an exemplary choice and that the actual number can vary from embodiment to embodiment and can be based in part on the energy of the radiation beam and the type of radiation (e.g., electron, photon, etc.). For example, for a lower energy beam (e.g., 4 MV), the high gradient region may be shallower than 3 cm and, as such, some embodiments may have radiation detector responses recorded within 2 cm or 1 cm of the water surface. Similarly, in embodiments where the beam energy is higher (e.g., 25 MV), rather than recording within 3 cm of the water surface, radiation detector responses may be recorded within 6 cm of the water surface while still sampling in the high-gradient region. In addition to considering penetration depth of a particular beam, the sampling region may also be determined through consideration of a potential or likely phantom tilt. For example, a higher potential tilt counsels in favor of recording data through a greater region from the expected water surface.

Accordingly, different embodiments may include moving the radiation detector (e.g., along a calibration path and/or measurement path) and recording a radiation detector response within 1 cm, 2 cm, 3 cm, 4 cm, 5 cm, 6 cm, etc., of the water surface. Such paths may include the entire high-gradient region, or a fraction of the high-gradient region, for example, approximately 50%, 75%, or 90% of the high gradient region.

Also, it is contemplated that some or all of the radiation detector responses may occur deeper than the high-gradient region, such as around 4 cm, 6 cm, 10 cm, 20 cm, etc. of the water surface. Similarly, radiation detector responses can be recorded at around 10%, 20%, 25%, 50%, 70%, or 90% of the maximum water depth or at those percentages of the extent of vertical travel along the vertical drive from the highest vertical position of the vertical drive. With the scanning system tilt determined, at 640, scanning system 10 can be controlled to move the radiation detector through one or more measurement paths that take into account the scanning system tilt. The measurement paths can be determined based on at least the first, second, and third radiation detector responses. As described below, particularly with reference to the FIG. 8, determination of a scanning system tilt provides the needed information to determine the appropriate measurement path to take into account the scanning system tilt.

The embodiment described above particularly notes that radiation detector response can be measured where it changes rapidly. Accordingly, in some embodiments, rather than using detector response data acquired where the detector response data changes slowly as a function of depth, the measurement path determination can be based on high-gradient regions of the first, second, and third radiation detector responses.

When referring to directions such as "horizontal" or "vertical," this is with reference to scanning system 10, and not to the central axis 78 of the radiation beam, the phantom, or the water surface in the phantom. Furthermore, "horizontal" or "vertical," as used herein, do not mean exactly vertical or horizontal, but rather describe generally horizontal or vertical (which, respectively, may be at a right angle to or in the direction relative to gravity or towards a water surface). Because, in some cases, the tilt of scanning system 10 may be small, movement by a vertical drive is still considered "vertical" and lateral movement, such as by the horizontal drive, may still be considered "horizontal." Furthermore, it is understood that any given directions need not be exact, and that deviations due to machine error or deviations in paths that do not affect the principles or methods described herein are considered sufficiently "horizontal" or "vertical."

As used herein, the term "calibration path" means any path that the radiation detector is moved along during a calibration process. However, the data taken along the calibration path can be used for actual measurement data, for example, as when performing quality assurance or any sort of non-calibration operations. As an example, radiation detector 38 can be moved along the three calibration paths, and once the scanning system tilt is accounted for, the data acquired along those calibration paths can be used as measurement data.

Further, the term "calibration" is intended to merely distinguish over other measurements that may be performed, for example, as part of radiation delivery system quality assurance (QA) procedure. In other words, a "calibration path" is a path used in determining a scanning system tilt and a "measurement path" is a path that can be executed while measuring the output of the radiation beam as part of QA. Both can be considered to be part of a "calibration," initialization, adjustment, or characterization of a radiation therapy delivery system. Finally, executing a "calibration path" does not require that a "calibration" be performed—as discussed further below, embodiments disclosed herein (with particular reference to FIG. 9) can allow for adjustment of scanning system 10 such that such that the scanning system is not tilted and no "calibration" to account for the tilt is necessary.

As used herein, the phrase "take into account the scanning system tilt" (or similar phrases) means applying one or more of a correction or adjustment to the motion or position of a radiation detector, or applying a modification or correction of received radiation detector data, such that the use of the scanning system behaves as if the scanning system was parallel to the water surface. However, when scanning system 10 is not actually tilted, then modifications or corrections to the operation of scanning system 10 may not be performed, or such corrections will be null corrections (i.e., adding zero or changing a measurement path slope by zero degrees).

Figure 7:
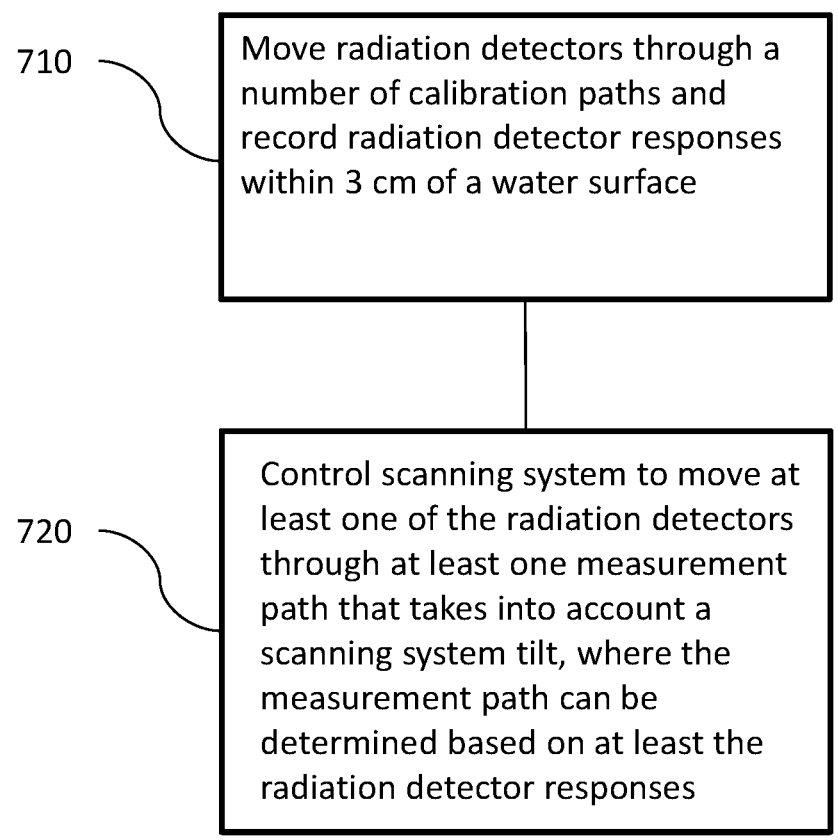
FIG. 7 is a process flow diagram describing an exemplary process for use of multiple radiation detectors to determine a scanning system tilt, in accordance with certain aspects of the present disclosure.

FIG. 7 is a process flow diagram describing use of multiple radiation detectors to determine a scanning system tilt, in accordance with certain aspects of the present disclosure.

In another embodiment, rather than repositioning a single detector and executing three calibration paths, more than one detector may be used, for example, to acquire some calibration paths in parallel. For example, three radiation detectors can be coupled to scanning system 10 such that with a single scan of the vertical drive the three calibration paths can be acquired. In general, scanning system 10 can include any number of radiation detectors and scanning system 10 can be configured to enable movement of the radiation detectors. As shown in FIG. 7, at 710, the radiation detectors can be moved through a number of calibration paths and a number of radiation detector responses can be recorded, for example, within 3 cm of a water surface. Also, at 720, the scanning system 10 can be controlled to move a radiation detector through at least one measurement path that takes into account a scanning system tilt. As before, the measurement path can be determined based on at least the radiation detector responses. Here, the measurement path can be determined similarly to the measurement path determination described above with reference to using a single radiation detector. Also, the radiation detector that is moved through the measurement path can be one of the radiation detectors moved through the calibration path. In other embodiments, the radiation detector that is moved through the measurement path can be a different radiation detector (e.g., separate from any that may have been used with the calibration paths). Though specifically discussed for this embodiment, it is contemplated that the radiation detector(s) used for measurement can be either the same used for calibration or can be different—for any of the embodiments described herein.

In yet another embodiment, for example when the scanning system 10 includes a ring drive, there can be two radiation detectors mounted on a diameter drive (e.g., on a horizontal drive along a diameter of the ring drive). A first vertical scan (acquiring two calibration paths) can then be acquired with two radiation detectors on the diameter drive. A second vertical scan can be acquired with the diameter drive after rotating the two radiation detectors to a different angle (acquiring another two calibration paths).

Figure 8:
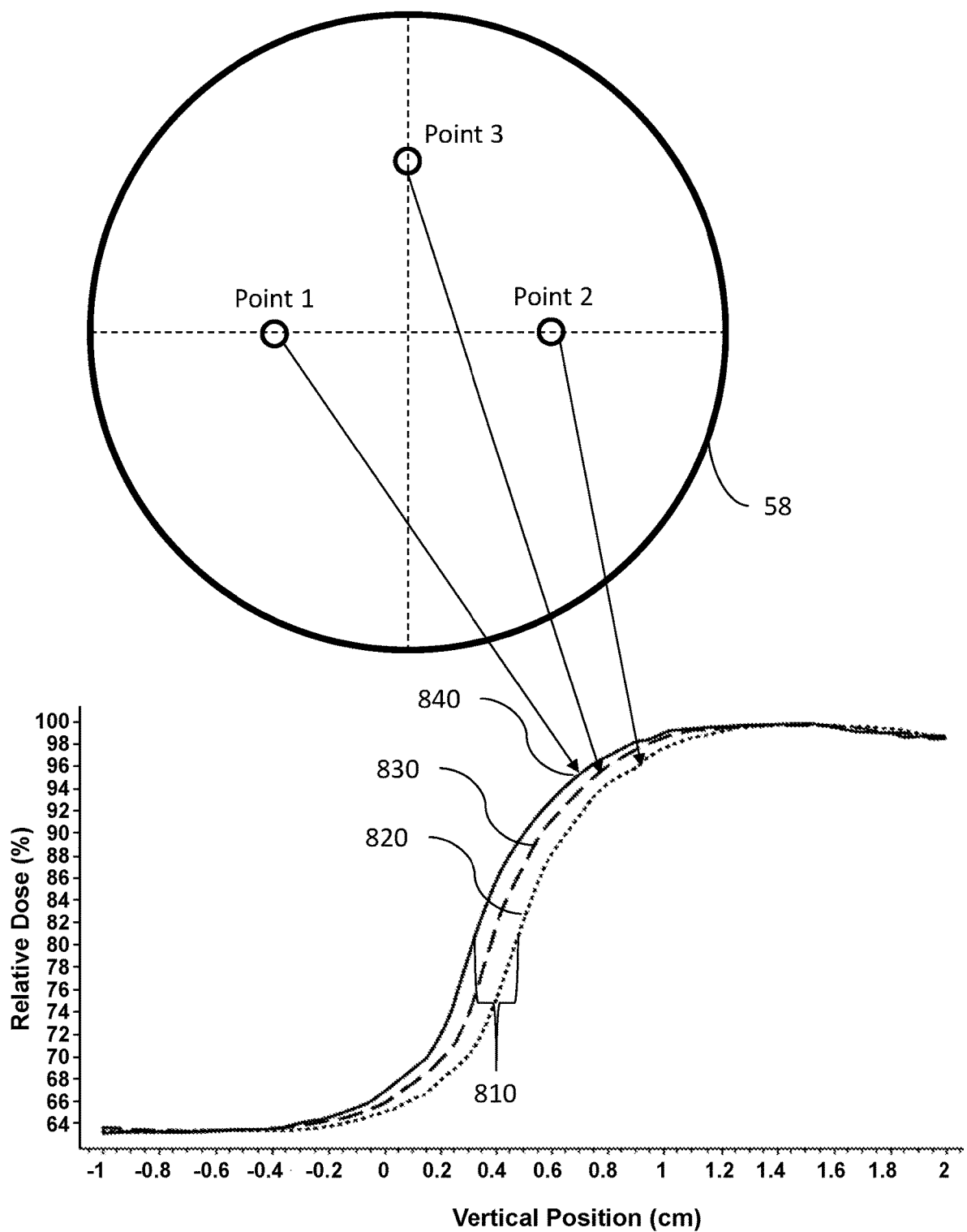
FIG. 8 is a simplified diagram illustrating an exemplary indication of offset in radiation detector responses caused by scanning system tilt, in accordance with certain aspects of the present disclosure.

FIG. 8 is a simplified diagram illustrating an offset in radiation detector responses caused by scanning system tilt, in accordance with certain aspects of the present disclosure.

Vertically scanning with a radiation detector when the scanning system 10 is tilted can result in an offset 810 of a radiation detector response profile from location to location (e.g., at different X-Y locations in the scanning system). As seen from the three exemplary radiation detector responses 820, 830, and 840, this offset is easiest to measure in the high-gradient region of the radiation detector response. Accordingly, as described in further detail below, a rapidly changing radiation detector response can facilitate accurate determination of scanning system tilt with fewer acquisition points.

In some cases, it can be assumed that the radiation field is uniform. However, in reality, this may not be the case and, in some embodiments, as shown, for example, in FIG. 8, the radiation detector responses can be normalized to their maximum values to allow for a variable fluence radiation field.

With (optionally) normalized radiation detector responses, determination of the scanning system tilt can include determining slopes of the points in the radiation detector responses according to the following expression:

$$m = \frac{n * \sum (x_i * y_i) - (\sum x_i * \sum y_i)}{n * \sum (x_i^2) - (\sum x_i)^2} \quad (2)$$

In Eq. 2, the summations are taken over data points (i) in the radiation detector responses around the location where the slope is being determined, e.g., resulting in three to five points in the sum, including the central point at the location where the slope is being calculated. In Eq. 2, $x_i$ is the position along the vertical axis (e.g. the vertical scan direction), $y_i$ is the value of the response at $x_i$, and n is the total number of data points in the summation.

For the radiation detector responses, a subset of the calculated slope data can be isolated or extracted, e.g., the three or five adjacent points including a central point at the location of maximum slope. The data subsets can be used to determine the offset between the radiation detector responses at a location of maximum slope, as described below.

The present disclosure describes several computational methods for determining offsets and the corresponding tilt. In one embodiment, functional fits can be performed to any two of the radiation detector responses in order to calculate slopes and offsets between them. For example, it can be seen from FIG. 8 that a significant portion of the radiation detector response can be well-fitted by a hyperbolic tangent. Similarly, some portions, for instance those in the steepest part of the high-gradient region, could be well-fitted by a line. Also, some portions of the radiation detector response may be fitted with a polynomial function. Such analytical expressions have corresponding features associated with them. For example, "features" of a linear fit are the slope and intercept. Similarly, features of a hyperbolic tangent can be various coefficients or constants defined in the fitting function. In addition to parameterizations, other quantities can be derived that can be used as "features." For example, regardless of what fitting function may be used, some "features" can describe a particular location or attribute of the radiation detector response. Determining the offset can be based on differences in any two radiation detector responses at the feature locations. Calculating feature locations can be based at least on the functional fits, with the feature locations corresponding to, for example, a maximum gradient location, an inflection point, a maximum curvature, a specific dose value, etc. In this way, a similar subset of data points around any defined feature of the functional fit can be used in a manner similar to that described with regard to using a location of maximum gradient.

The offset described above can be calculated based on any two (or optionally three) of the first radiation detector response, the second radiation detector response, and the third radiation detector response. With a set of normalized radiation detector responses, the offset between the radiation detector responses can be determined and, as described herein, the measurement path determination can then be based on at least the offset.

In one embodiment, the offset between two radiation detector responses can be determined by performing a least-squares minimization. In such an embodiment, one of the radiation detector responses can include a variable offset parameter added to the vertical position coordinate (referred to below as "z", and taken along the Z-axis of the scanning system). For example, such a minimization can include minimizing the following expression based on any two radiation detector responses, referred to below as curve 1 and curve 2:

$$\Sigma_{all\ points\ in\ curve2}(\text{Dose}_{curve1}(z\text{-offset})-\text{Dose}_{curve2}(z))^2 \quad (1)$$

Recall that from the above, the points used (e.g., in curves 1 and 2) can be the (e.g., 3-5) points determined to correspond to, for example, the location of maximum slope. In this way, the minimization need not be performed on the entire radiation detector responses and, by using this smaller and more relevant data subset, a result can be calculated using less computer memory and fewer processing cycles. One method of minimizing Eq. 1 can include performing a binary search over different values of the offset. Such a binary search can have a specified resolution, for example 0.01 mm. In general, the resolution can be smaller (or much smaller) than a gradient scale length of either of the radiation detector response curves (e.g., resolution<Δ(response)/(Δ (response)/unit length in the vertical direction)). Accordingly, the offset can be calculated between the three pairs of radiation detector responses 820 and 830, 830 and 840, and 820 and 840.

Recall that the offset is between two radiation detector response curves, taken at different X-Y locations in the phantom. The offset thus represents the change in detector response, not as a function of Z, but as a function of location (i.e., X and Y).

In the particular exemplary case illustrated herein, where two of the locations (taken here to be on the X axis, e.g., in the direction of the horizontal or diameter drives) are equidistant, with the third point on the Y-axis (perpendicular to the X-axis) and equidistant from two X locations, the scanning system tilt can be expressed in terms of the slope (or tilt) in the X direction and a slope (or tilt) in the Y direction.

Referring back to FIG. 8, for the example given herein where there are three radiation detector response curves, the offset between the pairs of curves can be referred to as: $offset_{12}$ (shown as element 810 and corresponding to the offset between responses measured at Point 1 and Point 2), $offset_{23}$ (between Point 2 and Point 3), and $offset_{13}$ (between Point 1 and Point 3).

The tilt in the X direction is $$\frac{offset\_x}{\Delta x},$$

which is the offset between the two X-axis points (or $offset_{12}$) divided by the total separation between the X-axis points (or X-coordinates of Point 1 and Point 2). The tilt in the Y direction is $$\frac{offset\_y}{\Delta y},$$

which is the average of $offset_{23}$ and $offset_{13}$, divided by the Y axis position of Point 3. With the above quantities, two tilt angles can be determined as:

$$X\_axis\_tilt = \left[atan\left(\frac{offset\_x}{\Delta x}\right)\right]^\circ, \text{ and}$$

$$Y\_axis\_tilt = \left[atan\left(\frac{offset\_y}{\Delta y}\right)\right]^\circ.$$

These angles (or any equivalent expression of the scanning system tilt) can be used for determination of measurement paths, physical correction of the scanning system, etc.

In one embodiment, X axis tilt and Y axis tilt can be displayed as angles to the user so they understand the physical alignment of scanning system 10. These slopes can also be used by the software to adjust the vertical positions of any step-by-step (or continuous motion with motor/drive synchronization) scan measurements made during actual testing/commissioning. For a measurement performed at a depth "z" (the depth z being determined at the center of the tank—i.e., the X,Y origin), the system's motors can be instructed to move both horizontally and vertically in order to stay parallel to the water surface. The adjusted vertical positions (Za) can be determined by the equation: Za=Z+(x*sin(X_axis_tilt))+(y*sin(Y_axis_tilt)).

As shown by the specific example above, in some embodiments, controlling the scanning system 10 movement through the measurement path can be based on at least one of the first, second, or third radiation detector responses as recorded in a high-gradient region of the corresponding first 820, second 830, or third 840 radiation detector responses. The measurement path can result, for example, in part from the adjusted vertical positions as described above.

In yet another embodiment, instead of, or in addition to, determining a pair of angles based on at least the offset, a normal vector can be calculated that represents a plane of the scanning system 10 (e.g., a plane that is parallel to the horizontal drive of the scanning system 10).

After the scanning system tilt has been determined, the measurement path can, for example, be determined based on at least the normal vector, or the pair of angles. The above-determined tilt can be used to determine the measurement path such that the radiation detector goes to the intended location relative not to scanning system 10 but instead relative to the water surface. As described above, any controlling or adjustment to the scanning system or the radiation detector can be done without determining the actual surface location of the water.

In another embodiment, system tilt can be accounted for by correcting detector responses/measurements performed during QA to account for a tilt when the measurement path has not been altered to proceed parallel to a water surface. For example, if, at a given location, a radiation detector response (e.g., in terms of current, voltage, counts, etc.) should be changing by 10%/cm in the X direction, but due to the scanning system tilt the change is only 9%/cm, then the radiation detector response can be corrected to add 1% to the radiation detector response after 1 cm of X travel based on a determination of system tilt in accordance with the teachings of the present disclosure. Such embodiments can thus include controlling the scanning system to move the radiation detector through a raw data path (which can be any path of radiation detector 38) and during movement of the detector along the raw data path, a raw data radiation detector response can be recorded. The raw data radiation detector response is the data from radiation detector 38, which may be inaccurate due to the tilt of scanning system 10. A corrected radiation detector response can then be provided based on at least an application of a correction function to the raw data radiation detector response. As described in the example above, after applying a correction function, the corrected radiation detector response is what the radiation detector would have recorded if scanning system 10 had not been tilted. A correction function can be, for example, values from a lookup table, an analytical formula, or any sort of data store that can be accessed to correct the raw data radiation detector response. Such an embodiment can be used with known or derived dose (or response) vs. depth data, provided from another calibration or determined based on the methods described herein.

Figure 9:
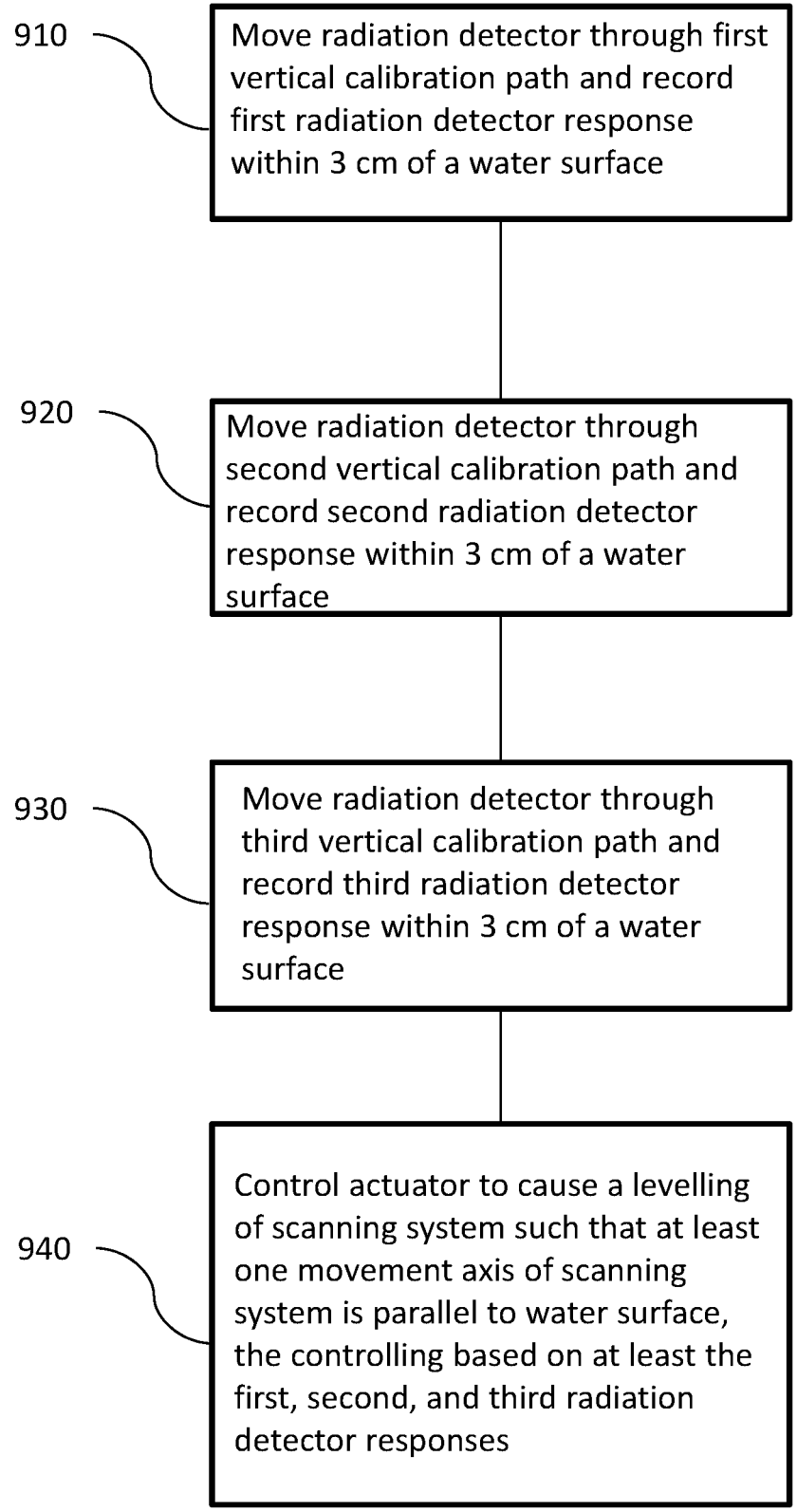
FIG. 9 is a process flow diagram describing an exemplary process for physical leveling of a scanning system, in accordance with certain aspects of the present disclosure.

FIG. 9 is a process flow diagram describing physical leveling of a scanning system 10, in accordance with certain aspects of the present disclosure.

In addition to performing an electronic leveling of the scanning system 10 by modifying movement of radiation detector, scanning system 10 can be physically leveled by correcting the scanning system tilt itself. This can include, for example, at 910, moving a radiation detector through a first vertical calibration path and recording a first radiation detector response, for example, within 3 cm of a water surface, at 920, moving a radiation detector through a second vertical calibration path and recording a second radiation detector response, for example, within 3 cm of the water surface, and, at 930, moving a radiation detector through a third vertical calibration path and recording a third radiation detector response, for example, within 3 cm of the water surface.

Then, in one embodiment, at 940, an actuator can be controlled to cause a leveling of the scanning system 10 such that at least one movement axis of the scanning system 10 is parallel to the water surface. The controlling can be based on at least the first, second, and third radiation detector responses. As used herein, the term "actuator" means any mechanical device for moving or controlling something. For example, an actuator can be a spring-actuated adjustment mechanism, pneumatic lift, gear train, belt system, screw adjustment mechanism, etc. Such actuators can be incorporated into, for example, a leveling table, tripod, etc., that can be manually adjusted or computer controlled to cause a reduction in scanning system tilt.

Also, similar to that described above, some embodiments can include calculating an offset based on any two of the first radiation detector response, the second radiation detector response, and the third radiation detector response. Then, the controlling of the actuator to cause the leveling of the scanning system 10 can be further based on the offset.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include embodiment in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The embodiments set forth in the foregoing description do not represent all embodiments consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The embodiments described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A computer program product comprising a non-transitory, machine-readable medium storing instructions which, when executed by at least one programmable processor, cause the at least one programmable processor to perform operations comprising:
moving a radiation detector through a first vertical calibration path and recording a first radiation detector response within 3 cm of a water surface;
moving the radiation detector through a second vertical calibration path and recording a second radiation detector response within 3 cm of the water surface;
moving the radiation detector through a third vertical calibration path and recording a third radiation detector response within 3 cm of the water surface; and
controlling a scanning system to move the radiation detector through at least one measurement path that takes into account a scanning system tilt, the at least one measurement path determined based on at least the first, second, and third radiation detector responses.

2. The computer program product of claim 1, wherein the measurement path determination is based on high-gradient regions of the first, second, and third radiation detector responses.

3. The computer program product of claim 1, the operations further comprising:
calculating an offset based on any two of the first radiation detector response, the second radiation detector response, and the third radiation detector response; and
wherein the measurement path determination is based on at least the offset.

4. The computer program product of claim 3, wherein the offset is calculated in a high-gradient region of the first, second, or third radiation detector responses.

5. The computer program product of claim 3, the operations further comprising:
performing functional fits to the any two radiation detector responses;
calculating feature locations based on at least the functional fits; and
determining the offset based on differences in the any two radiation detector responses at the feature locations.

6. The computer program product of claim 5, wherein the feature locations correspond to at least one of a maximum gradient location, an inflection point, a maximum curvature, and a specific dose value.

7. The computer program product of claim 3, the operations further comprising:
calculating, based on at least the offset, a normal vector representing a plane of the scanning system; or
calculating, based on at least the offset, a pair of angles representing the plane of the scanning system; and
wherein the measurement path determination is based on at least the normal vector or the pair of angles.

8. A computer program product comprising a non-transitory, machine-readable medium storing instructions which, when executed by at least one programmable processor, cause the at least one programmable processor to perform operations comprising:
moving a radiation detector through a first vertical calibration path and recording a first radiation detector response within 3 cm of a water surface;
moving the radiation detector through a second vertical calibration path and recording a second radiation detector response within 3 cm of the water surface;
moving the radiation detector through a third vertical calibration path and recording a third radiation detector response within 3 cm of the water surface;
calculating a correction function based on at least the first, second, and third radiation detector responses;
controlling the scanning system to move the radiation detector through a raw data path and recording, during the movement of the radiation detector along the raw data path, a raw data radiation detector response; and
providing a corrected radiation detector response based on at least an application of the correction function to the raw data radiation detector response.

9. A computer program product comprising a non-transitory, machine-readable medium storing instructions which, when executed by at least one programmable processor, cause the at least one programmable processor to perform operations comprising:
moving a plurality of radiation detectors through a plurality of calibration paths and recording a plurality of radiation detector responses within 3 cm of a water surface; and
controlling a scanning system to move a radiation detector through at least one measurement path that takes into account a scanning system tilt, the at least one measurement path determined based on at least the plurality of radiation detector responses.

10. A computer program product comprising a non-transitory, machine-readable medium storing instructions which, when executed by at least one programmable processor, cause the at least one programmable processor to perform operations comprising:
moving a radiation detector through a first vertical calibration path and recording a first radiation detector response within 3 cm of a water surface;
moving the radiation detector through a second vertical calibration path and recording a second radiation detector response within 3 cm of the water surface;
moving the radiation detector through a third vertical calibration path and recording a third radiation detector response within 3 cm of the water surface; and
controlling an actuator to cause a leveling of a scanning system such that at least one movement axis of the scanning system is parallel to the water surface, the controlling based on at least the first, second, and third radiation detector responses.

11. The computer program product of claim 10, the operations further comprising:
calculating an offset based on any two of the first radiation detector response, the second radiation detector response, and the third radiation detector response, and wherein the controlling of the actuator to cause the leveling of the scanning system is further based on the offset.

* * * * *